(12) United States Patent
Fujiwara

(10) Patent No.: US 11,051,684 B2
(45) Date of Patent: Jul. 6, 2021

(54) ENDOSCOPE LIGHT SOURCE DEVICE

(71) Applicant: OLYMPUS CORPORATION, Hachioji (JP)

(72) Inventor: Kazuto Fujiwara, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 66 days.

(21) Appl. No.: 16/693,339

(22) Filed: Nov. 24, 2019

(65) Prior Publication Data

US 2020/0093359 A1 Mar. 26, 2020

Related U.S. Application Data

(63) Continuation of application No. PCT/JP2018/014847, filed on Apr. 9, 2018.

(30) Foreign Application Priority Data

Jun. 2, 2017 (JP) .............................. JP2017-110067

(51) Int. Cl.
  *A61B 1/06* (2006.01)
  *G02B 6/32* (2006.01)
  *G02B 27/14* (2006.01)
  *G02B 27/30* (2006.01)
  (Continued)

(52) U.S. Cl.
  CPC .......... *A61B 1/0669* (2013.01); *A61B 1/0638* (2013.01); *A61B 1/07* (2013.01);
  (Continued)

(58) Field of Classification Search
  CPC ....... A61B 1/0669; A61B 1/0638; A61B 1/07; A61B 1/06; G02B 27/0916; G02B 6/262;
  (Continued)

(56) References Cited

U.S. PATENT DOCUMENTS 9,482,870 B2 11/2016 Hanano
10,130,245 B2 11/2018 Takato et al.
(Continued)

FOREIGN PATENT DOCUMENTS

EP 2865936 A1 4/2015
EP 3096176 A1 11/2016
(Continued)

OTHER PUBLICATIONS

International Search Report (ISR) dated Jun. 19, 2018 (and English translation thereof), issued in International Application No. PCT/JP2018/014847.
Written Opinion of the International Searching Authority dated Jun. 19, 2018 issued in International Application No. PCT/JP2018/014847.

*Primary Examiner* — Leslie C Pascal
(74) *Attorney, Agent, or Firm* — Holtz, Holtz & Volek PC

(57) ABSTRACT

An endoscope light source device includes: a plurality of solid-state light sources; a plurality of collimating lenses that respectively collimate light beams emitted from the plurality of solid-state light sources into substantially parallel light beams; a multiplexing optical member that multiplexes the light beams that have been collimated into substantially parallel light beams by the plurality of collimating lenses; at least one diaphragm disposed between at least one of the plurality of solid-state light sources and a corresponding at least one of the plurality of collimating lenses; and a focusing lens that focuses multiplexed light beams from the plurality of solid-state light sources and causes the light beams to enter an end surface of a light guide of an endoscope, wherein the at least one diaphragm blocks more peripheral light as an optical path length from each of the plurality of solid-state light sources to the focusing lens becomes smaller.

10 Claims, 20 Drawing Sheets

(51) Int. Cl.
  *G02B 27/09* (2006.01)
  *G02B 6/26* (2006.01)
  *A61B 1/07* (2006.01)

(52) U.S. Cl.
  CPC .............. *G02B 6/262* (2013.01); *G02B 6/32* (2013.01); *G02B 27/0916* (2013.01); *G02B 27/141* (2013.01); *G02B 27/30* (2013.01)

(58) Field of Classification Search
  CPC ........ G02B 6/32; G02B 27/141; G02B 27/30; G02B 19/0061; G02B 19/0014; G02B 23/2469; G02B 6/0006; F21S 2/00; F21V 11/08
  See application file for complete search history.

(56) References Cited

U.S. PATENT DOCUMENTS

| | | | |
|---|---|---|---|
| 2015/0098242 A1 | 4/2015 | Hanano | |
| 2016/0256042 A1 | 9/2016 | Takato et al. | |
| 2018/0052075 A1* | 2/2018 | Seno | .................. G01M 11/0235 |

FOREIGN PATENT DOCUMENTS

| | | | |
|---|---|---|---|
| JP | 2005342431 A | 12/2005 | |
| JP | 2006026128 A | 2/2006 | |
| JP | 2006087764 A | 4/2006 | |
| JP | 2012014853 A | 1/2012 | |
| JP | 2014007057 A | 1/2014 | |
| JP | 2014161639 A | 9/2014 | |
| JP | 5897224 B2 | 3/2016 | |

* cited by examiner

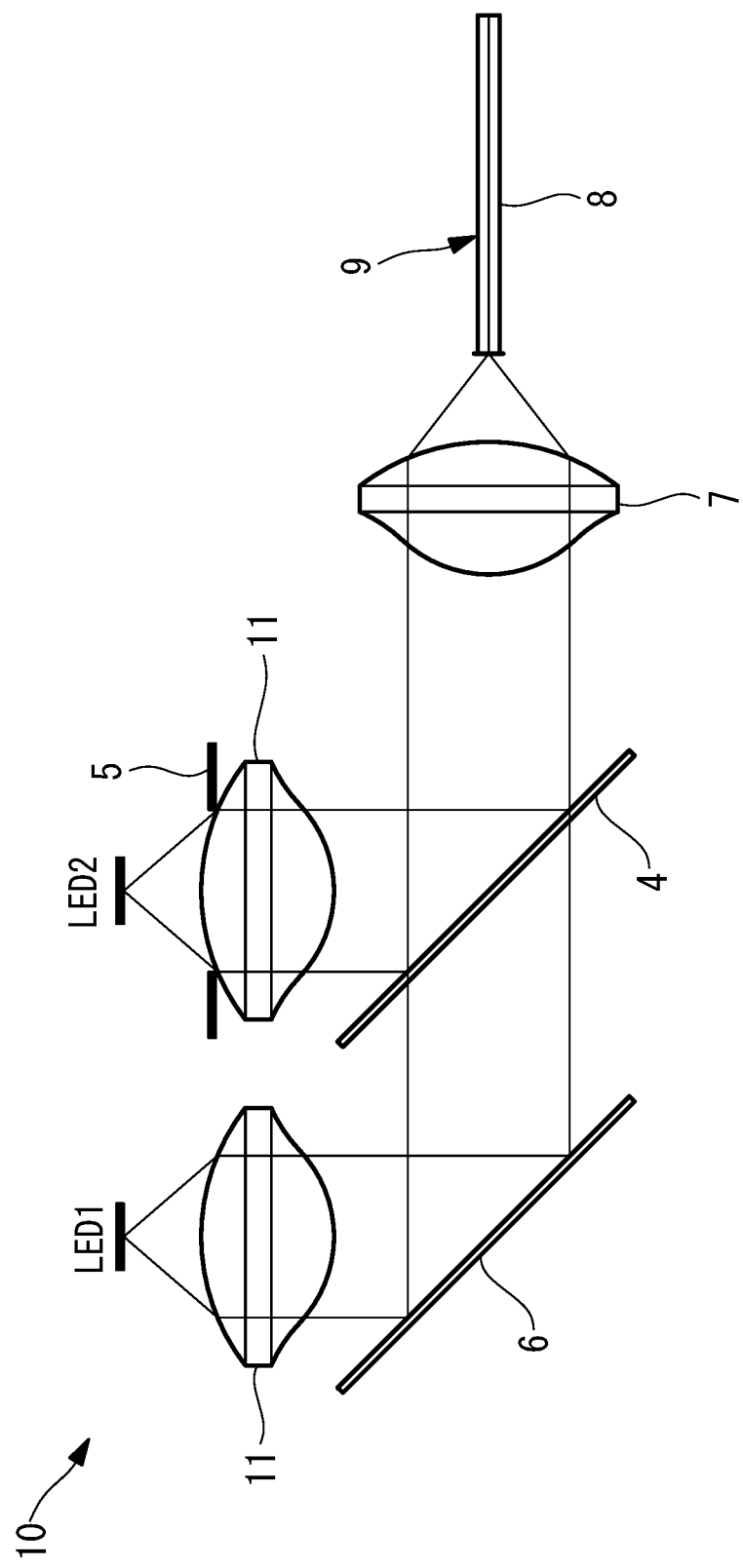

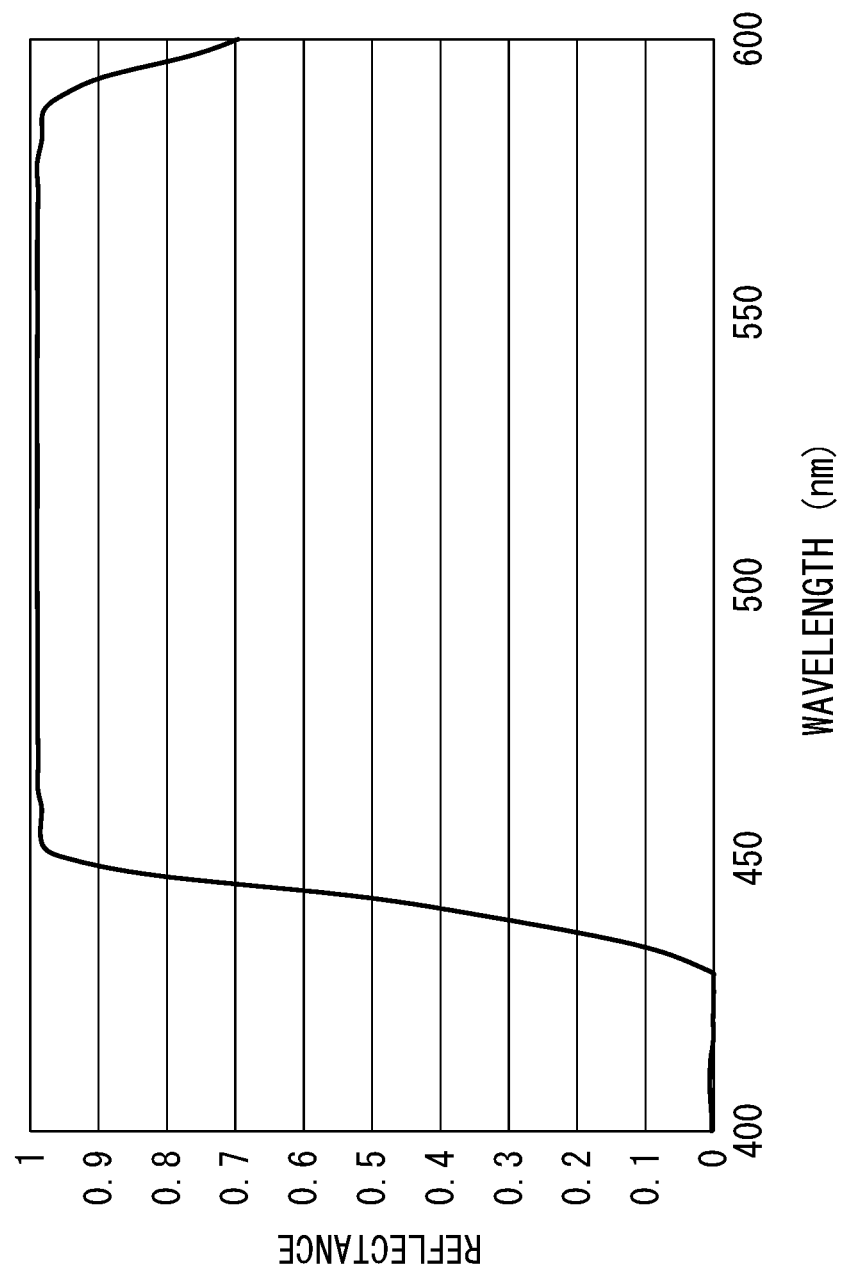

ENDOSCOPE LIGHT SOURCE DEVICE

CROSS-REFERENCE TO RELATED APPLICATIONS

This is a continuation of International Application PCT/JP2018/014847, with an international filing date of Apr. 9, 2018, which is hereby incorporated by reference herein in its entirety. This application claims the benefit of Japanese Patent Application No. 2017-110067, the content of which is incorporated herein by reference.

TECHNICAL FIELD

The present invention relates to an endoscope light source device.

BACKGROUND ART

There is known a light source device that emits broadband illuminating light obtained by collimating light beams from multiple semiconductor light sources that respectively emit light beams having different wavelengths and multiplexing the collimated light beams (for example, see PTL 1).

CITATION LIST

Patent Literature

{PTL 1} Japanese Unexamined Patent Application, Publication No. 2014-7057

SUMMARY OF INVENTION

An aspect of the present invention is directed to an endoscope light source device including plurality of solid-state light sources; a plurality of collimating lenses that respectively collimate light beams emitted from the plurality of solid-state light sources into substantially parallel light beams; a multiplexing optical member that multiplexes the light beams that have been collimated into substantially parallel light beams by the plurality of collimating lenses; at least one diaphragm disposed between at least one of the plurality of solid-state light sources and a corresponding at least one of the plurality of collimating lenses; and a focusing lens that focuses light beams from the plurality of solid-state light sources multiplexed by the multiplexing optical member and causes the light beams to enter an end surface of a light guide of an endoscope, wherein the at least one diaphragm blocks more peripheral light as an optical path length from each of the plurality of solid-state light sources to the focusing lens becomes smaller.

Another aspect of the present invention is directed to an endoscope light source device including: a plurality of solid-state light sources; a plurality of collimating lenses that respectively collimate light beams emitted from the plurality of solid-state light sources into substantially parallel light beams; a multiplexing optical member that multiplexes the light beams that have been collimated into substantially parallel light beams by the plurality of collimating lenses; at least one diaphragm disposed between at least one of the plurality of solid-state light sources and a corresponding at least one of the collimating lenses; and a focusing lens that focuses light beams from the plurality of solid-state light sources multiplexed by the multiplexing optical member and causes the light beams to enter an end surface of a light guide of an endoscope, wherein the at least one diaphragm has a different aperture size for each combination of one of the plurality of solid-state light sources and a corresponding one of the plurality of collimating lenses, and, as an optical path length from each of the plurality of solid-state light sources to the focusing lens becomes smaller, the aperture size of the at least one diaphragm becomes smaller.

Another aspect of the present invention is directed to an endoscope light source device including: a plurality of solid-state light sources; a plurality of collimating lenses that respectively collimate light beams emitted from the plurality of solid-state light sources into substantially parallel light beams; a multiplexing optical member that multiplexes the light beams that have been collimated into substantially parallel light beams by the plurality of collimating lenses; at least one diaphragm disposed between at least one of the plurality of solid-state light sources and a corresponding at least one of the plurality of collimating lenses; and a focusing lens that focuses light beams from the plurality of solid-state light sources multiplexed by the multiplexing optical member and causes the light beams to enter an end surface of a light guide of an endoscope, wherein a distance between the at least one diaphragm and a corresponding at least one of the plurality of solid-state light sources is different for each combination of one of the plurality of solid-state light sources and a corresponding one of the collimating lenses, and as an optical path length from each of the solid-state light source to the focusing lens becomes smaller, the distance from the at least one diaphragm to a corresponding at least one of the plurality of solid-state light source becomes larger.

BRIEF DESCRIPTION OF DRAWINGS

FIG. 1 is a schematic diagram illustrating an endoscope light source device according to one embodiment of the present invention.

FIG. 16 is a graph illustrating a reflectance characteristic of a dichroic mirror on the longest optical path in the endoscope light source device illustrated in FIG. 14.

DESCRIPTION OF EMBODIMENTS

Figure 2A:
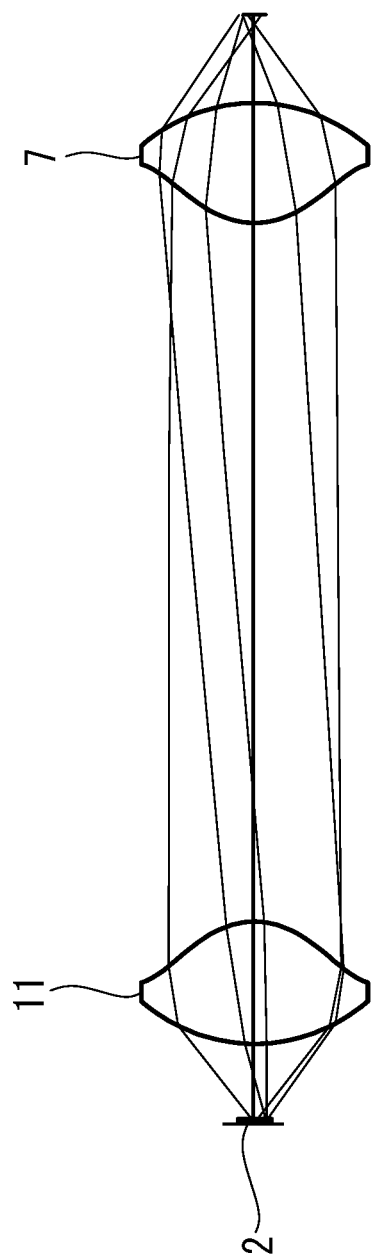
FIG. 2A is a diagram illustrating light beams from respective parts of an LED, in which, as a reference example of the endoscope light source device illustrated in FIG. 1, no diaphragm is provided, and the shorter optical path is extended in a straight line.

An endoscope light source device 10 according to one embodiment of the present invention will now be described with reference to the drawings.

As illustrated in FIG. 1, the endoscope light source device 10 according to the present embodiment includes multiple LEDs (solid-state light sources) 1 and 2 that respectively emit light beams having different wavelengths, multiple collimating lenses 11 that collimate the light beams emitted from the LEDs 1 and 2 into substantially parallel light beams, a dichroic mirror (multiplexing optical member) 4 that multiplexes the light beams that have been collimated into substantially parallel light beams by the collimating lenses 11, and a diaphragm (light-level-adjusting mechanism) 5 disposed between the LED 2 on the shorter optical path and the collimating lens 11. In the drawings, reference sign 6 denotes a mirror.

A first light beam emitted from the LED 1 on the longer optical path is collimated into a substantially parallel light beam by a collimating lens 11, is then deflected by the mirror 6, passes through the dichroic mirror 4, is focused through a focusing lens 7, and enters an incident end of a light guide 8 of a scope 9 of an endoscope.

Meanwhile, a second light beam emitted from the LED 2 on the shorter optical path is collimated into a substantially parallel light beam by a collimating lens 11, is then deflected by the dichroic mirror 4 so as to be multiplexed with the first light beam, is focused through the focusing lens 7, and enters the incident end of the light guide 8 of the scope 9 of the endoscope.

Figure 2B:
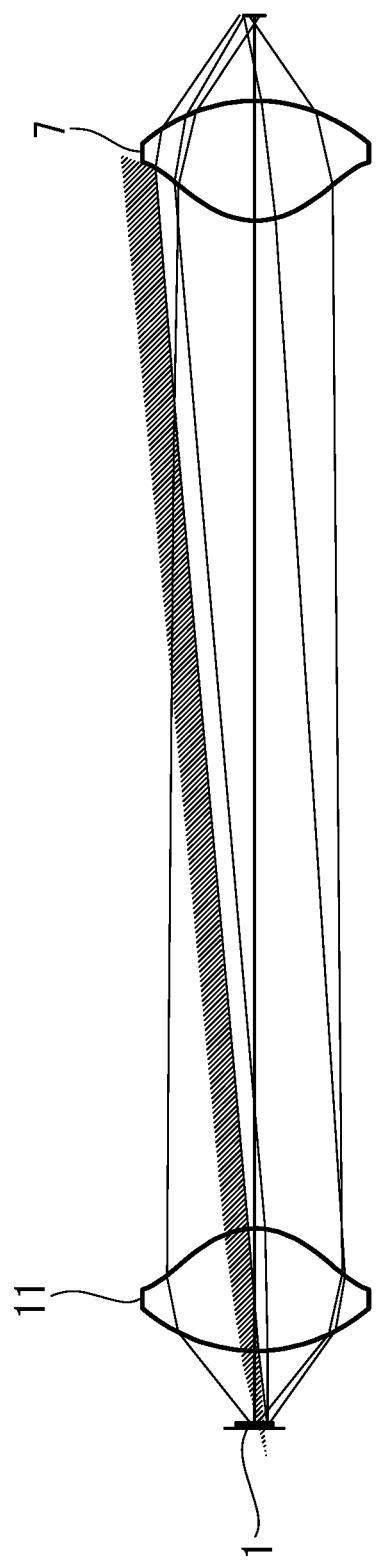
FIG. 2B is a diagram illustrating light beams from respective parts of an LED, in which, as a reference example of the endoscope light source device illustrated in FIG. 1, the longer optical path is extended in a straight line.
Figure 3:
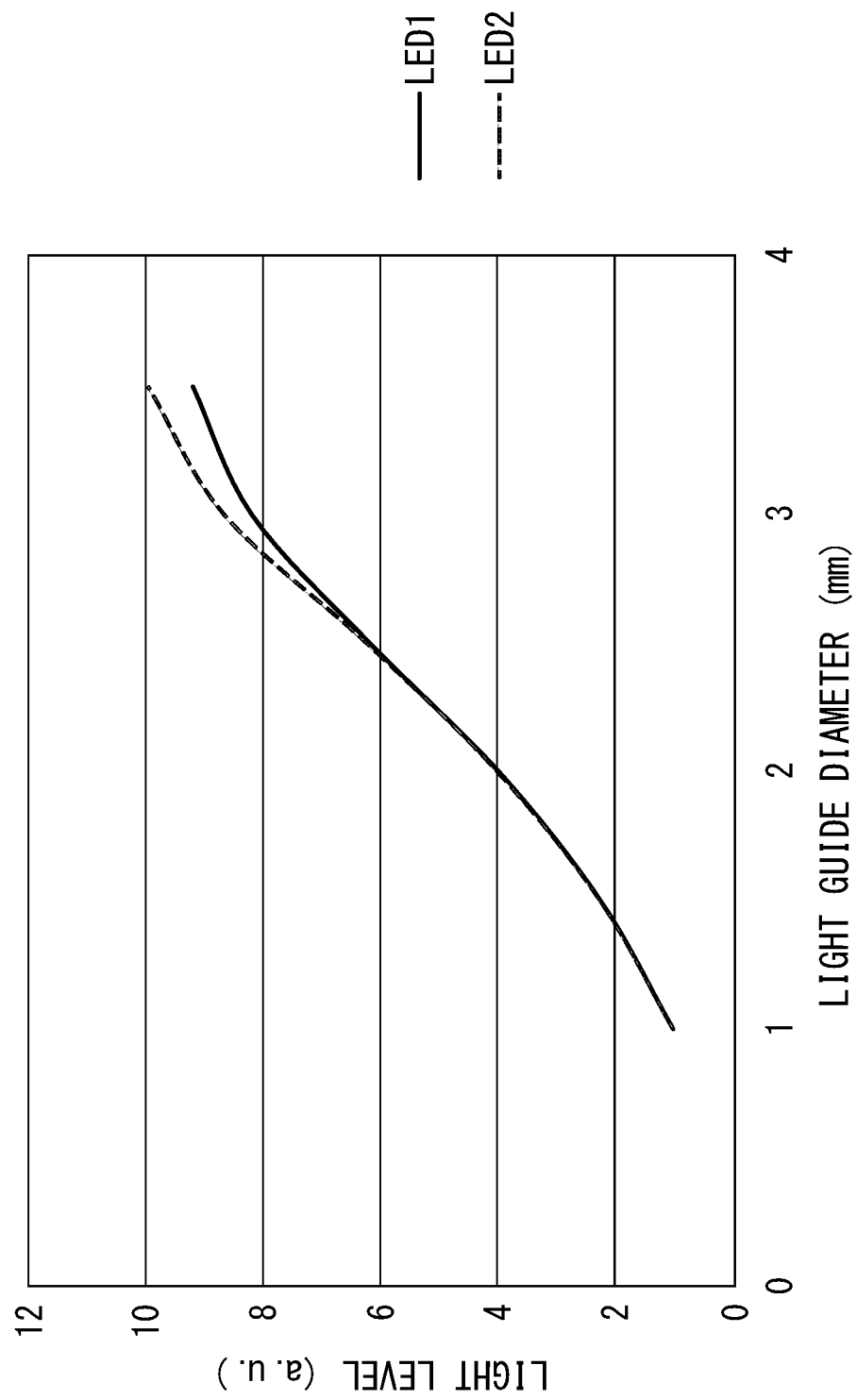
FIG. 3 is a graph illustrating the relationship between the light guide diameter and the light-level balance of the light beam emitted from the endoscope in the cases illustrated in FIGS. 2A and 2B.

In this case, since the LEDs 1 and 2 have certain sizes the collimating lenses 11 cannot generate perfectly collimated light beams from the light beams emitted from the LEDs 1 and 2. Compared to the case in which the optical path length is small, as illustrated in FIG. 2A, more peripheral light (the shaded portion in the drawing) is clipped by the focusing lens 7 as the optical path becomes longer, as illustrated in FIG. 2B. As a result, if a scope 9 equipped with a light guide 8 so thick as to allow peripheral light to enter is installed, the first light beam, which travels a larger optical path length and has peripheral light clipped by the focusing lens 7, exhibits a lower light level than the second light beam, which travels a smaller optical path length, as illustrated in FIG. 3, unless the diaphragm 5 is provided.

Figure 4:
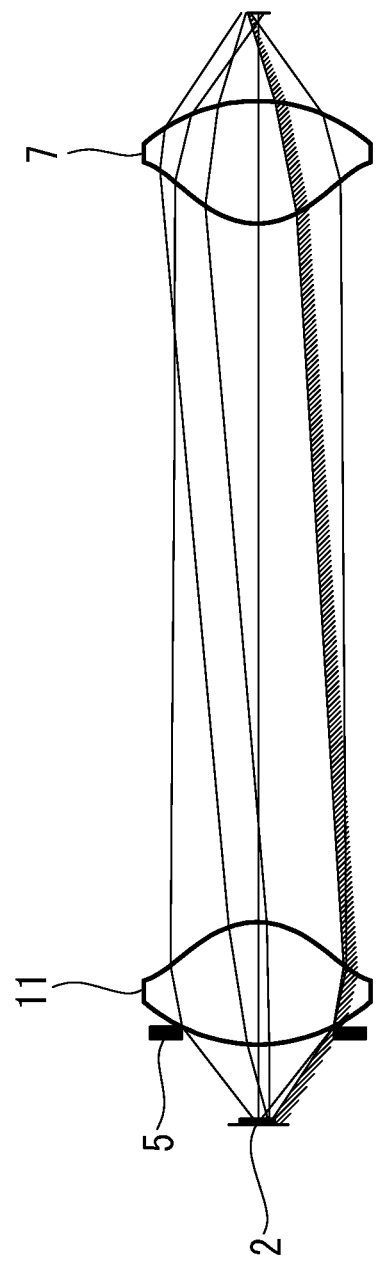
FIG. 4 is a diagram illustrating light beams from respective parts of an LED, in which the shorter optical path in the endoscope light source device illustrated in FIG. 1 is extended in a straight line.
Figure 5:
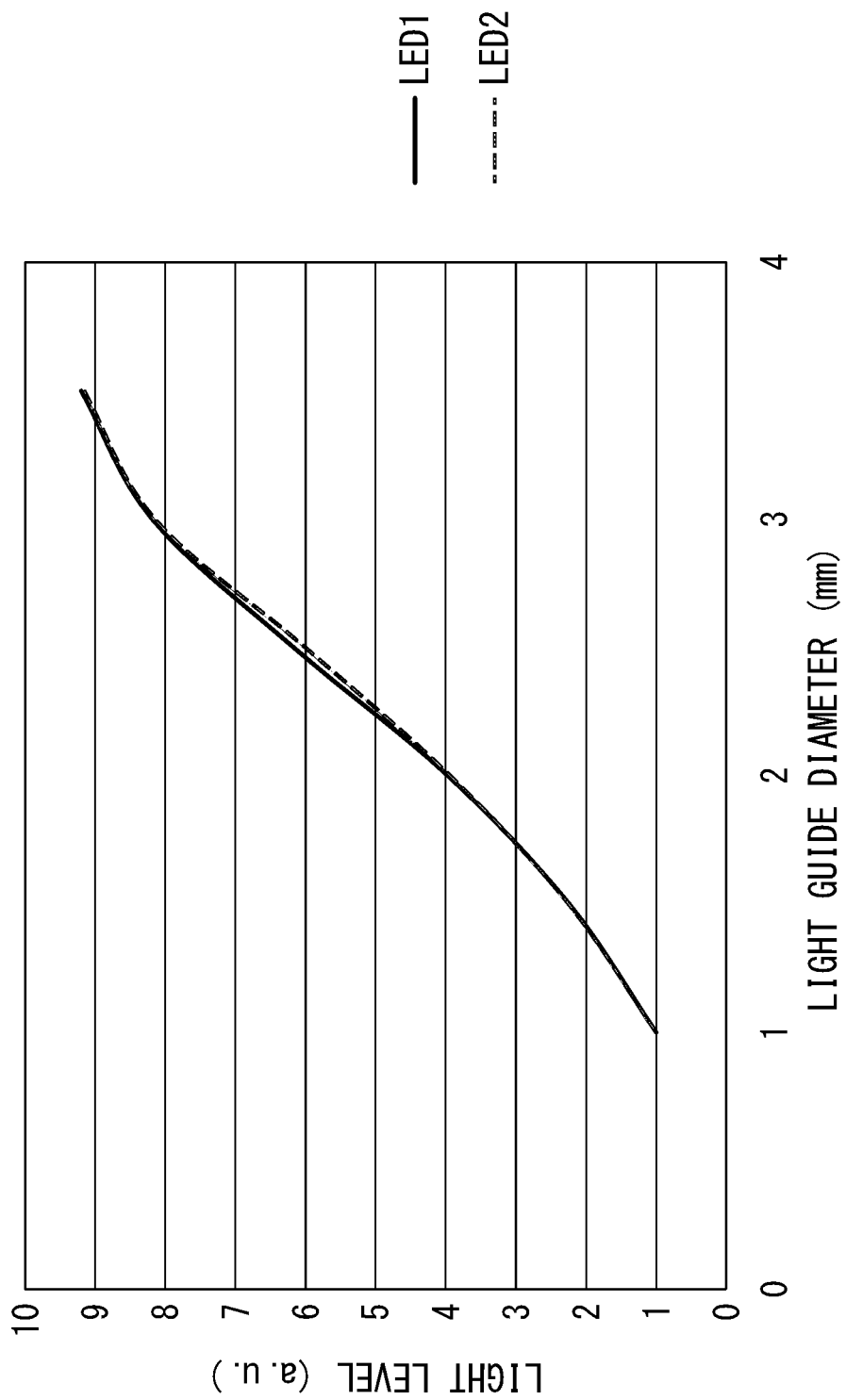
FIG. 5 is a graph illustrating the relationship between the light guide diameter and the light-level balance of the light beam emitted from the endoscope in the cases illustrated in FIGS. 3 and 2B.

In contrast, in the endoscope light source device 10 of the present embodiment, the diaphragm 5, which blocks the peripheral light in the second light beam, is disposed between the LED 2 and the collimating lens 11 on the shorter optical path. Thus, as illustrated in FIG. 4, the arrangement may be made to block the peripheral light in the second light beam in advance by appropriately adjusting the aperture area of the diaphragm 5. In other words, even when a scope 9 equipped with a light guide 8 so thick as to allow even the peripheral light to enter is installed, degradation of the light-level balance of the first light beam, which has traveled a larger optical path length and has the peripheral light clipped by the focusing lens 7, can be prevented, as illustrated in FIG. 5.

Conversely, when a scope 9 equipped with a light guide 8 so thin that peripheral light cannot enter is installed, only light on the axis enters the incident end of the light guide 8. Thus, as illustrated in FIGS. 3 and 5, irrespective of the optical path length, a uniform light-level balance can be achieved without being affected by the diaphragm 5.

The diaphragm 5 preferably satisfies conditional formula (1) below:

$$\phi/L \geq 2NA\beta/\sqrt{(1-(NA\beta)^2)} \quad (1)$$

where $\phi$ represents the aperture size of the diaphragm 5,

NA represents the numerical aperture of the light guide 8, $\beta$ represents the absolute value of the paraxial magnification when the LED 2 forms an image in the light guide 8, and L represents the optical path length between the LED 2 and the diaphragm 5.

The process leading to conditional formula (1) will now be described.

When NA of the light guide 8 is assumed to be NAlg, it is efficient for the optical system to perform focusing at NAlg. The light above NAlg cannot be taken into the light guide 8, constitutes a loss, and is converted into thermal energy.

Here, when the area of the emission surface is represented by Sled, the light-source-side NA of the light to be taken into the light guide 8 is represented by NAled, and the image forming area of the focusing surface is represented by Sled', the following conditional formula is established since the etendue is preserved.

$$\pi \times Sled \times NAled^2 \pi \times Sled' \times NAlg^2 \quad (2)$$

Here, in order for the aforementioned formula to be true even when the diaphragm 5 having the aperture size $\phi$ is placed on the LED 2 side, the light beam at NA on the LED 2 side must not be clipped. In order to do so, the following conditional formula must be established by using the distance L between the LED 2 and the diaphragm 5.

$$(\phi/2)/\sqrt{(L^2+(\phi/2)^2)} \geq NAled \quad (3)$$

When conditional formula (2) is substituted into conditional formula (3), formula (4) is obtained.

$$\pi \times Sled \times (\phi/2)^2/(L^2+(\phi/2)^2) \geq \pi \times Sled' \times NAlg^2 \quad (4)$$

Here, when the absolute value β of the paraxial lateral magnification of the optical system is used, the following is obtained:

$$Sled' = \beta^2 \times Sled \quad (5)$$

Conditional formula (1) can be obtained by substituting formula (5) into formula (4) and transforming the resulting formula.

It should be noted that when the aperture size φ of the diaphragm 5 is below conditional formula (1), the light distribution becomes narrow; however, as long as the following conditional formula (6) is satisfied, an endoscopic image can achieve light distribution characteristics acceptable for observation.

$$\phi/L \geq 1.5 NA\beta/\sqrt{(1-(NA\beta)^2)} \quad (6)$$

Here, the difference in distribution of light emitted from the scope 9 between when conditional formula (1) is satisfied and when conditional formula (6) is satisfied was confirmed.

Assuming that the aperture size φ of the diaphragm 5 is 22 mm, the distance L between the LED 2 and the diaphragm 5 is 12.55 mm, the absolute value β of the paraxial magnification of the optical system is 0.98, and the numerical aperture NA of the light guide 8 is 0.5, conditional formula (1) is satisfied.

Here, the aperture size φ of the diaphragm 5 that satisfies conditional formula (6) is calculated as follows:

φ=13.68 mm

Figure 6:
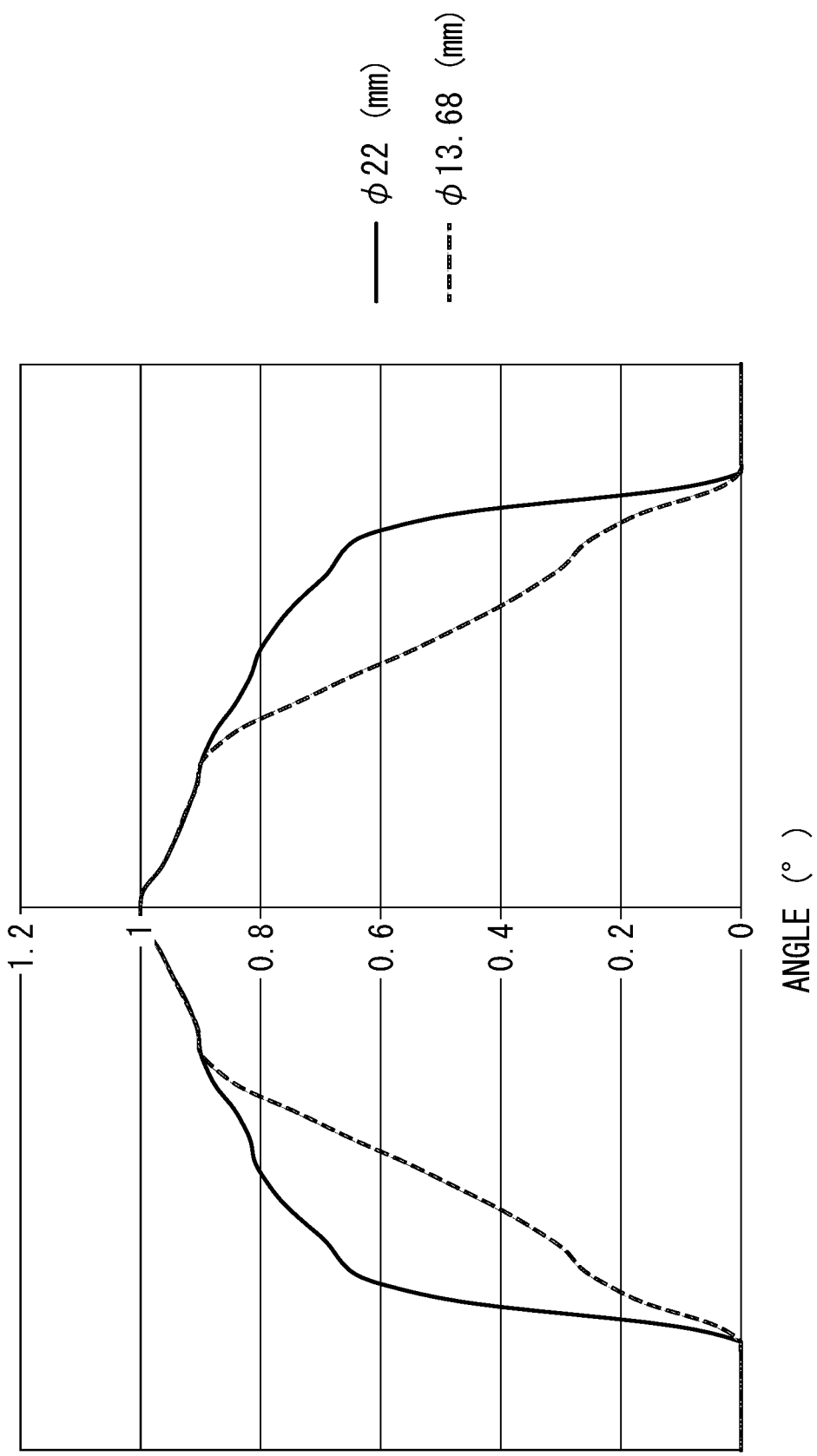
FIG. 6 is a graph illustrating light distributions of the light source emitted light when mathematical formula (1) and (6) are satisfied.

The light distributions of the light source emitted light when the aperture size φ of the diaphragm 5 is 22 mm and when φ is 13.68 mm are shown in FIG. 6.

Figure 7:
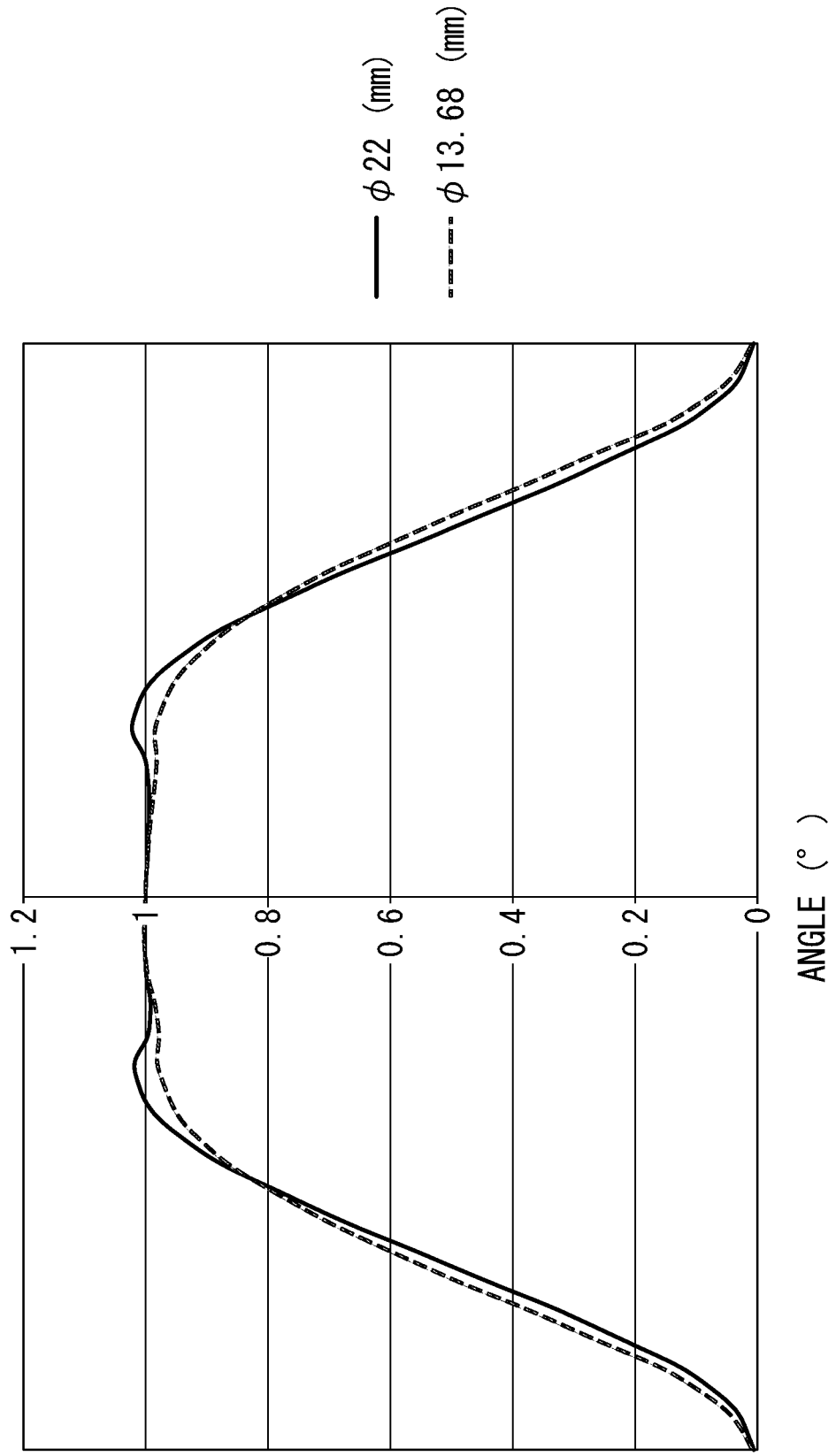
FIG. 7 is a graph illustrating the distribution of light emitted from the endoscope in the case illustrated in FIG. 6.

When the light distribution of the light source emitted light is as shown in FIG. 6, the calculated light distribution from the endoscope is as shown in FIG. 7.

For reference, the lens data of Example 1 described in Japanese Patent No. 05897224 were used for the illuminating optical system of the endoscope.

According to FIG. 7, there is no difference in light distribution (the range that can be illuminated) between when conditional formula (1) is satisfied and when conditional formula (6) is satisfied; thus, observation can be carried out satisfactorily when conditional formula (6) is satisfied.

In the present embodiment, the case in which light beams from two LEDs 1 and 2 are multiplexed has been described; however, the same may apply to the case in which three or more light beams from three or more LEDs 1, 2, and 3 are to be multiplexed. In such a case, as the optical path lengths from the LEDs 2 and 3 decrease, the aperture size of the diaphragm 5 is decreased to block more peripheral light. In this manner, even when the light guide diameter of the installed scope 9 is increased, the issue of degradation of the light-level balance of the light from the LED 1 on the longer optical path can be avoided.

A diaphragm 5 may also be placed between the LED 1 and the collimating lens 11 on the longest optical path.

Figure 8:
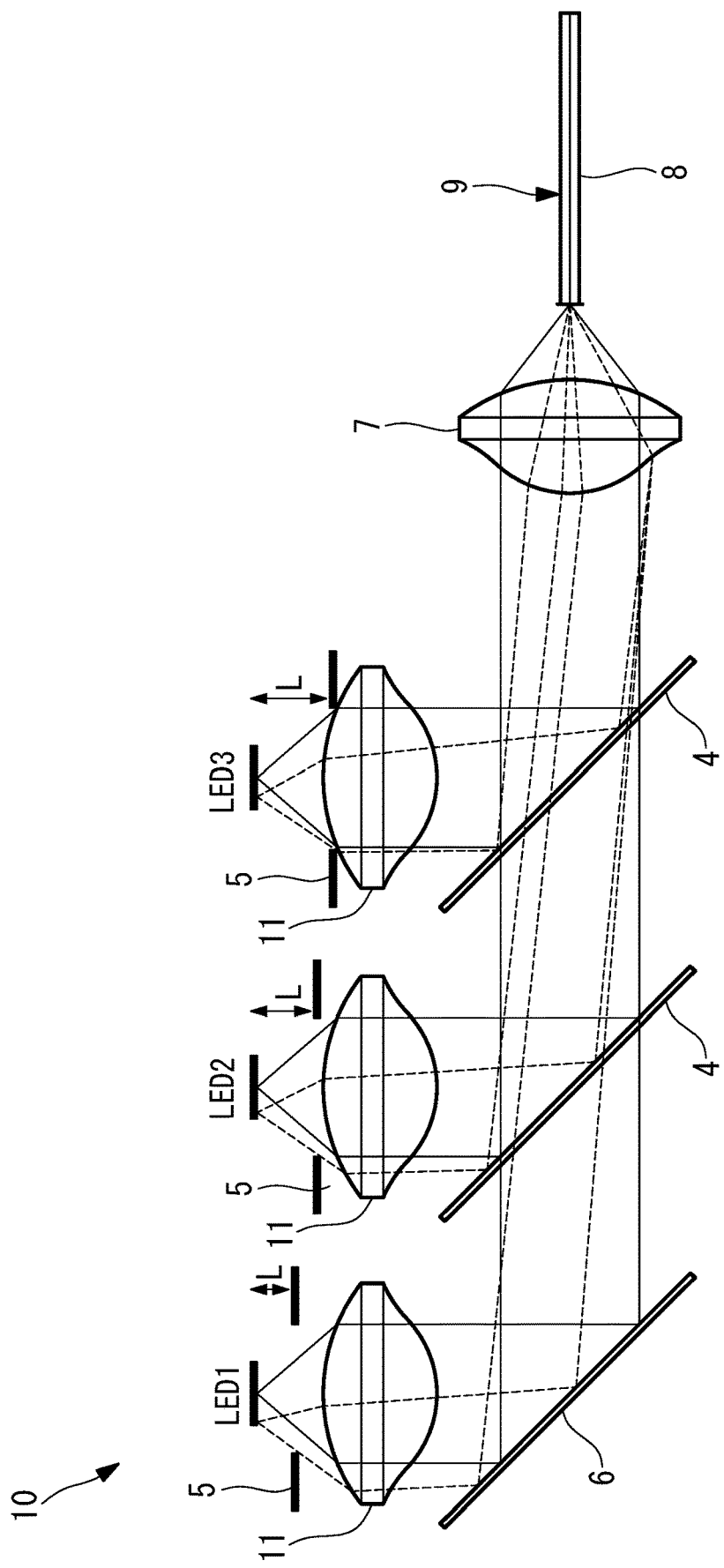
FIG. 8 is a diagram illustrating a modification of the endoscope light source device illustrated in FIG. 1.

Furthermore, in the present embodiment, the aperture size of the diaphragm 5 is changed to adjust the quantity of the emitted peripheral light. Alternatively, as illustrated in FIG. 8, the distances L between the LEDs 1, 2, and 3 and the diaphragms 5 may be changed so as to be different from one another. More peripheral light can be blocked by making the distances L between the LEDs 1, 2, and 3 and the diaphragms 5 decrease as the optical paths lengths from the LEDs 1, 2, and 3 become smaller.

In this manner, there is an advantage in that diaphragms 5 having the same shape can be used for all of the LEDs 1, 2, and 3, and thus the cost can be reduced.

First Embodiment

A first embodiment of the endoscope light source device 10 according to the present embodiment will now be described.

Figure 9:
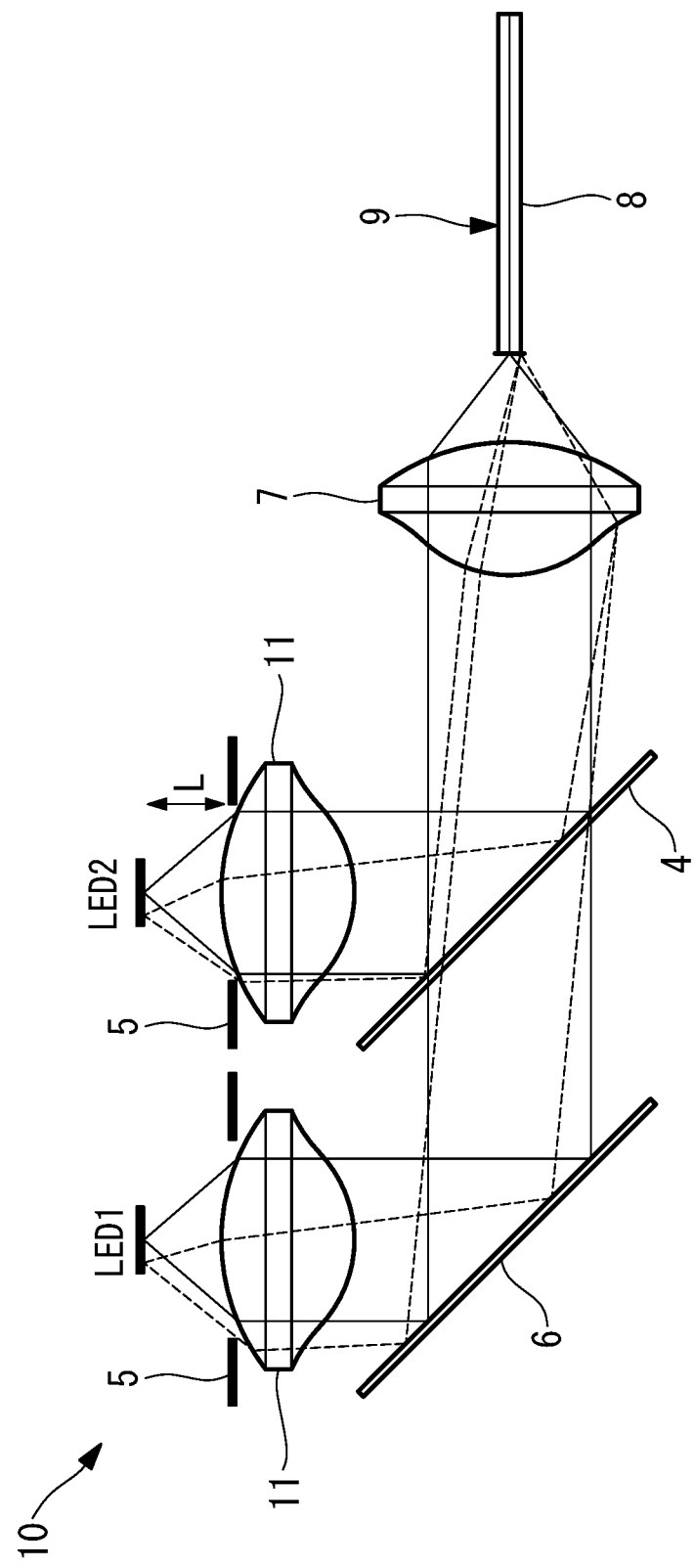
FIG. 9 is a diagram illustrating a first embodiment of the endoscope light source device illustrated in FIG. 1.

In this embodiment, as illustrated in FIG. 9, two LEDs 1 and 2 are provided, a diaphragm 5 is disposed between the LED 1 and the corresponding collimating lens 11, and another diaphragm 5 is disposed between the LED 2 and the corresponding collimating lens 11.

Figure 10A:
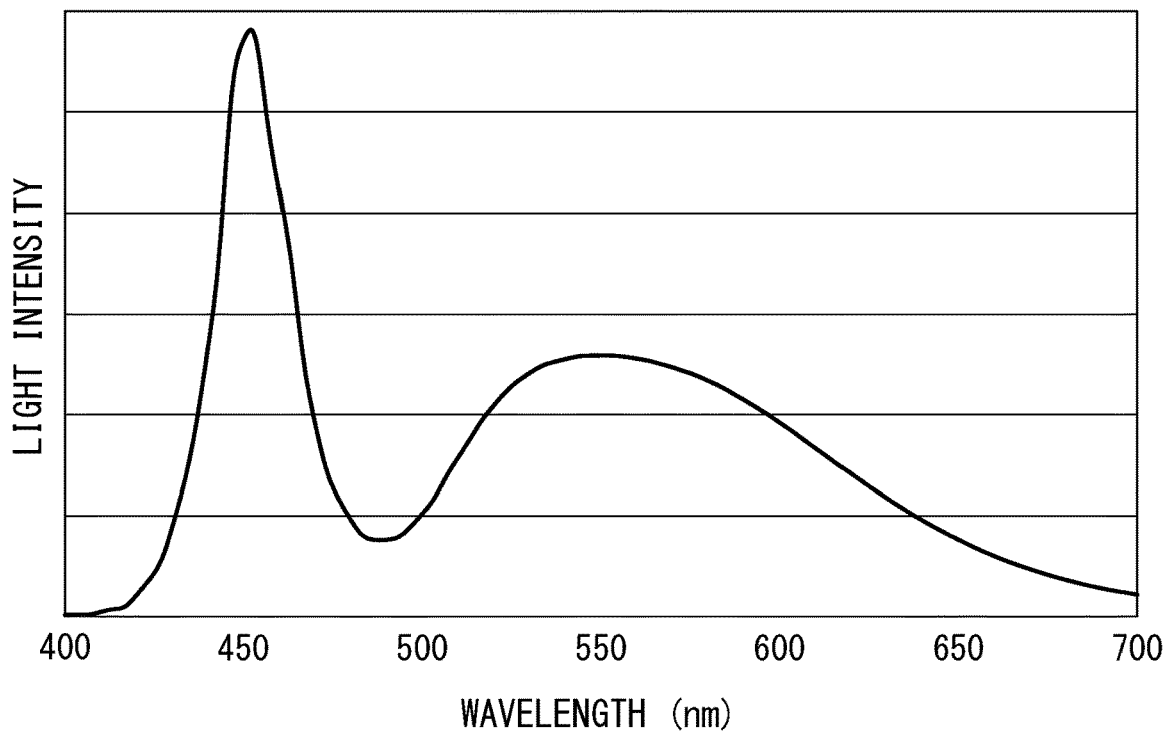
FIG. 10A is a graph illustrating a spectral characteristic of an LED on the longer optical path in the endoscope light source device illustrated in FIG. 9.
Figure 10B:
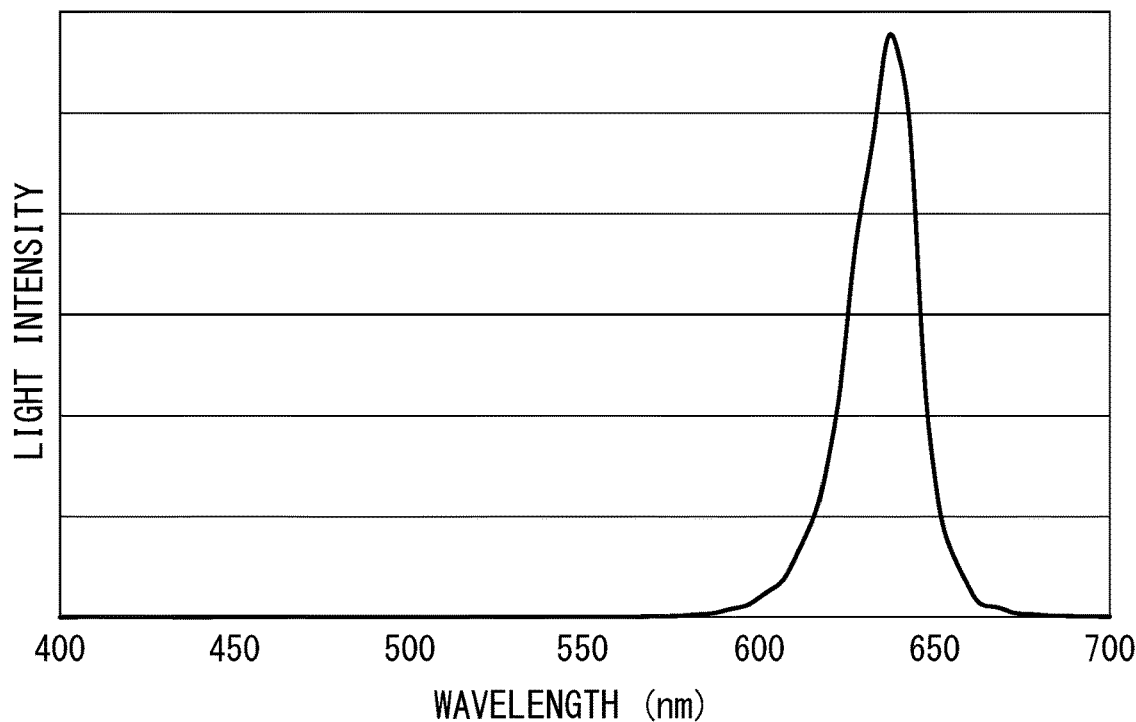
FIG. 10B is a graph illustrating a spectral characteristic of an LED on the shorter optical path in the endoscope light source device illustrated in FIG. 9.
Figure 11:
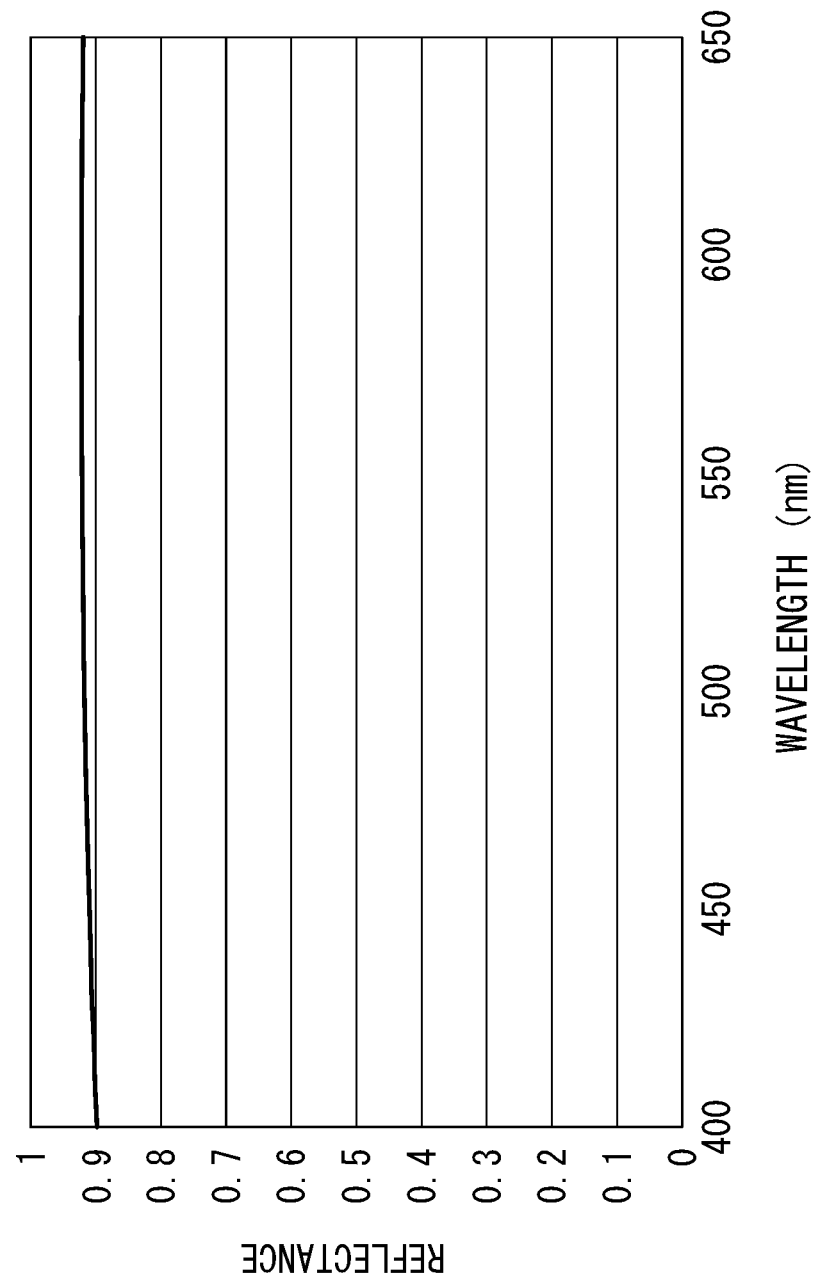
FIG. 11 is a graph illustrating a reflectance characteristic of a mirror of the endoscope light source device illustrated in FIG. 9.
Figure 12:
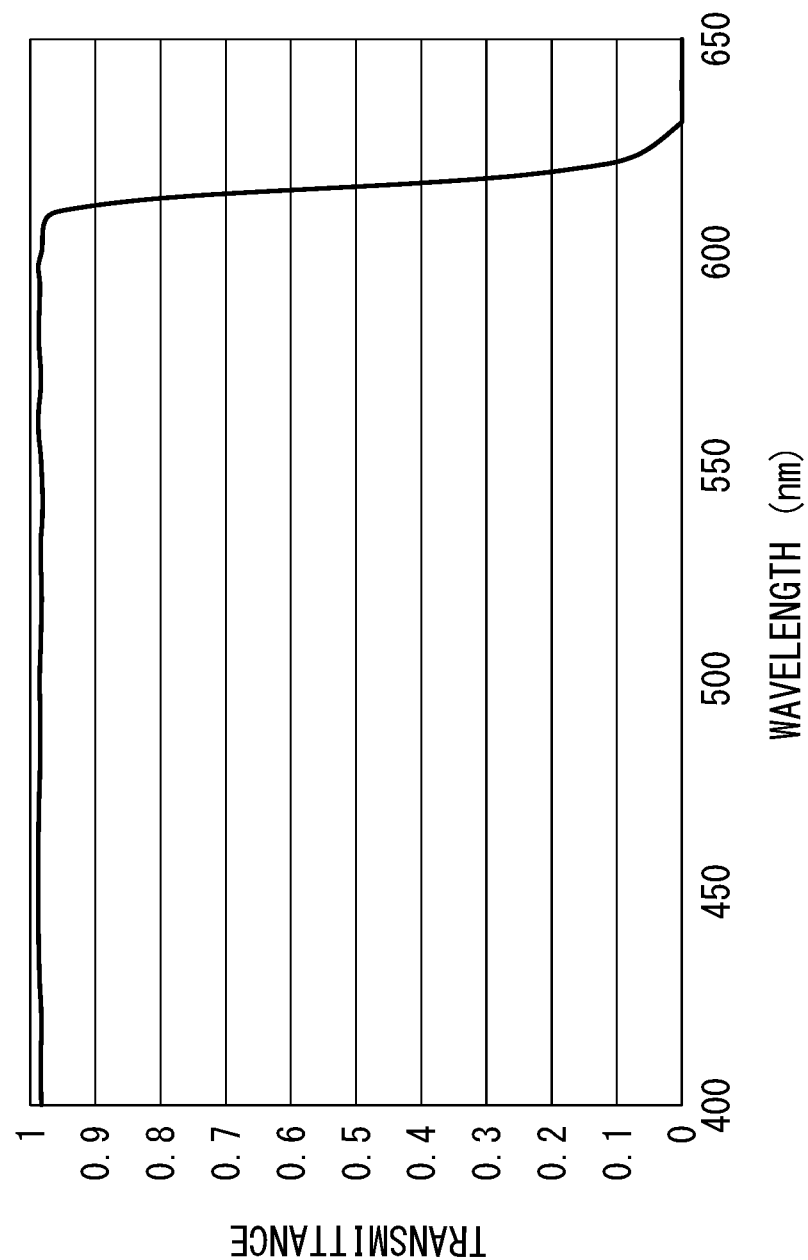
FIG. 12 is a graph illustrating a transmittance characteristic of a dichroic mirror of the endoscope light source device illustrated in FIG. 9.
Figure 13:
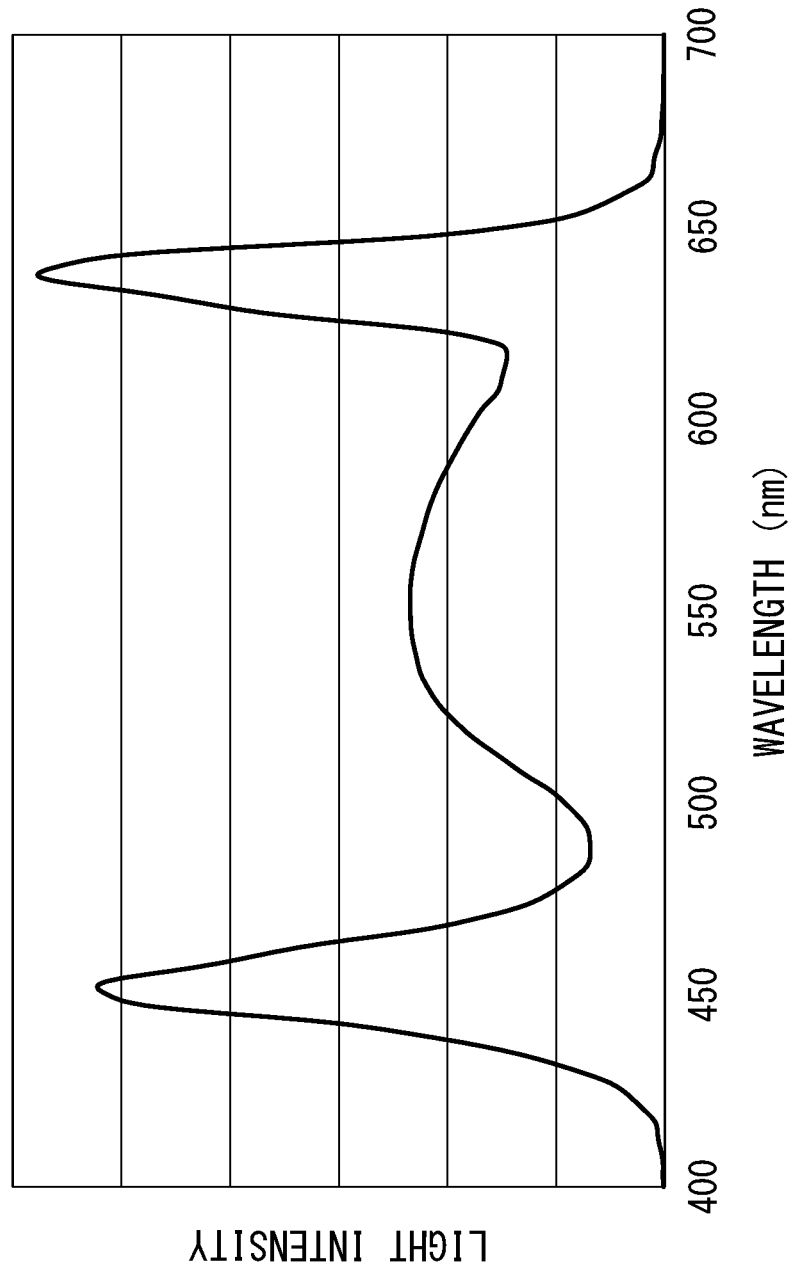
FIG. 13 is a graph illustrating a spectral characteristic of a light source emitted light of the endoscope light source device illustrated in FIG. 9.

The LEDs respectively having spectral characteristics shown in FIGS. 10A and 10B are used as LEDs 1 and 2, a mirror having a reflectance characteristic shown in FIG. 11 is used as the mirror 6, a dichroic mirror having a transmittance characteristic shown in FIG. 12 is used as the dichroic mirror 4, and the light source emitted light has a spectral characteristic shown in FIG. 13.

The aperture size φ of the diaphragm 5 placed on the longer optical path is 34 mm, the distance L is 12.55 mm, the paraxial magnification absolute value β is 0.94, and the numerical aperture NA of the light guide fiber of the endoscope is 0.5. In this manner, φ/L=2.71 and $1.5NA\beta/\sqrt{(1-(NA\beta)^2)}=1.02$. Thus, conditional formula (6) is satisfied.

The aperture size φ of the diaphragm 5 placed on the shorter optical path is 22 mm, the distance L is 12.55 mm, the paraxial magnification absolute value β is 0.98, and the numerical aperture NA of the light guide fiber of the endoscope is 0.5. In this manner, φ/L=1.75, and $1.5NA\beta/\sqrt{(1-(NA\beta)^2)}=1.10$. Thus, conditional formula (6) is satisfied.

Second Embodiment

A second embodiment of the endoscope light source device 10 according to the present embodiment will now be described.

Figure 14:
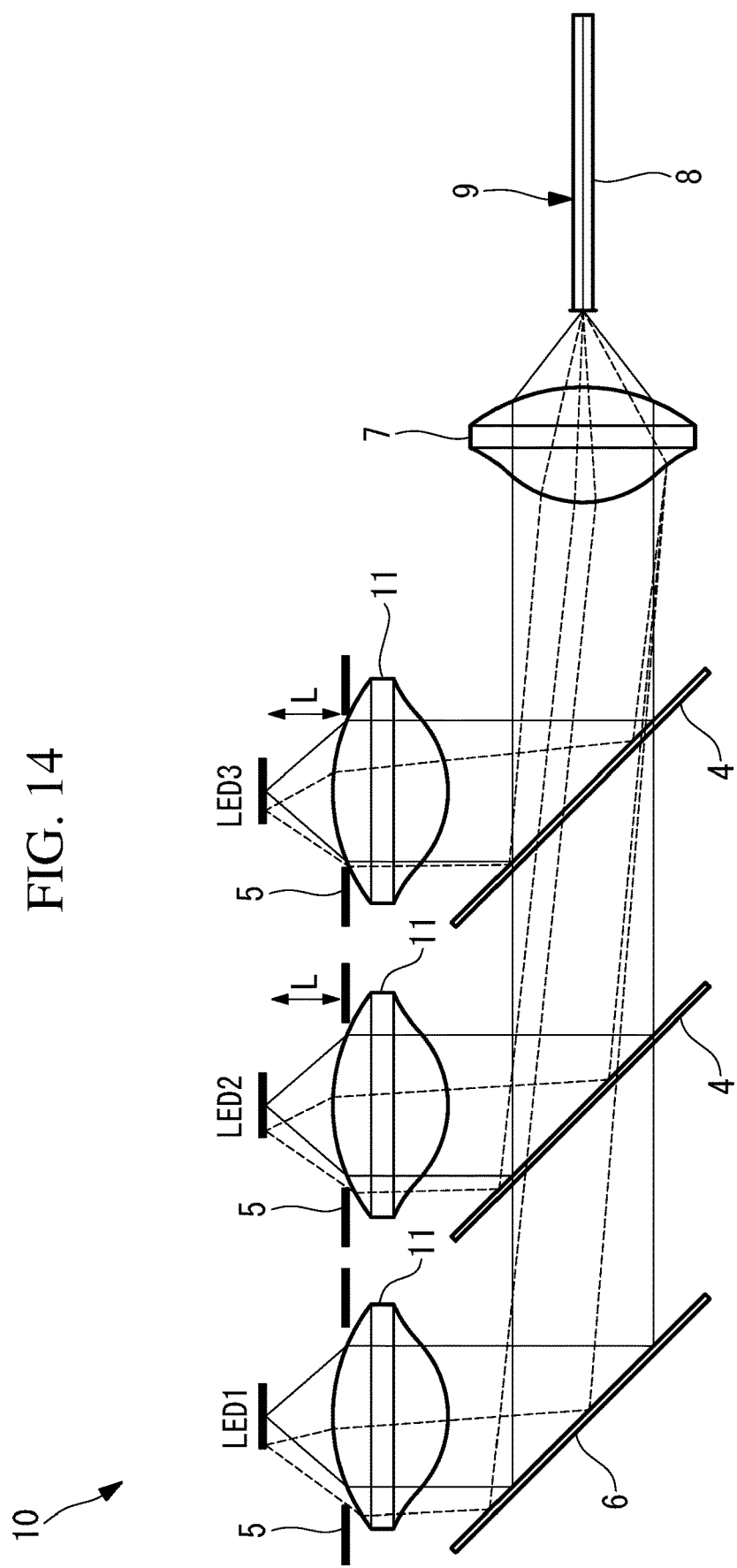
FIG. 14 is a diagram illustrating a second embodiment of the endoscope light source device illustrated in FIG. 1.

In this embodiment, as illustrated in FIG. 14, three LEDs 1, 2, and 3 are provided, a diaphragm 5 is disposed between each of the LEDs 1, 2, and 3 and the corresponding collimating lens 11.

Figure 15A:
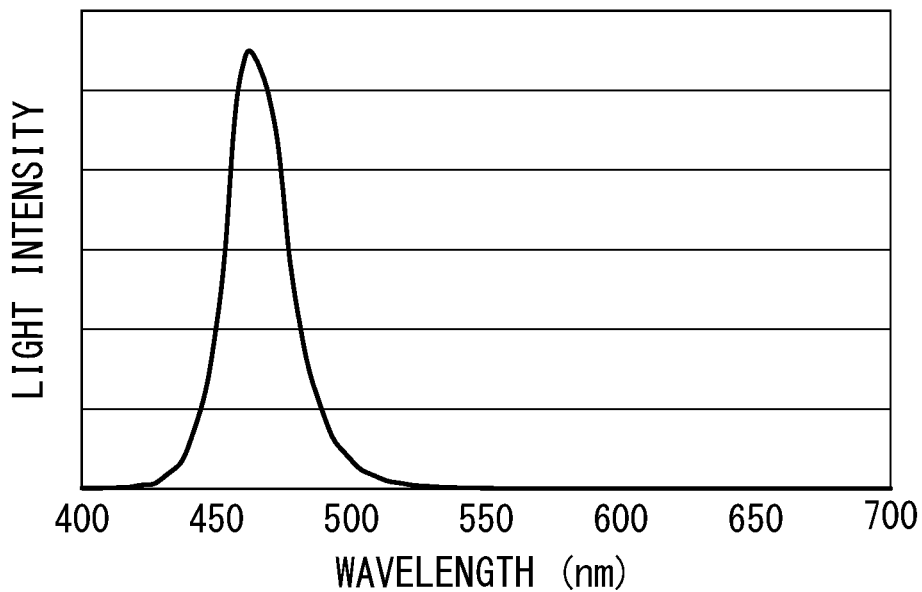
FIG. 15A is a graph illustrating a spectral characteristic of an LED on the longest optical path in the endoscope light source device illustrated in FIG. 14.
Figure 15B:
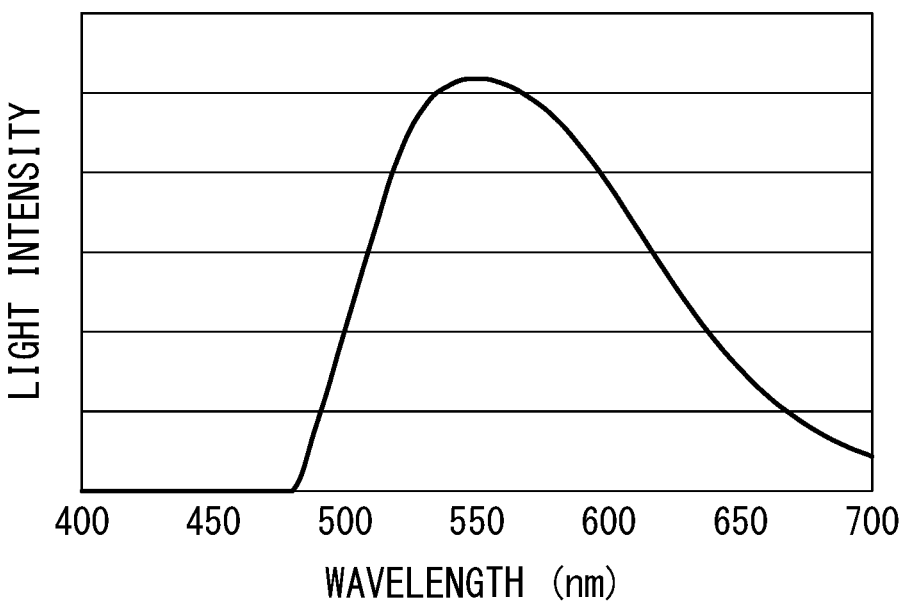
FIG. 15B is a graph illustrating the spectral characteristic of an LED on the second-longest optical path in the endoscope light source device illustrated in FIG. 14.
Figure 15C:
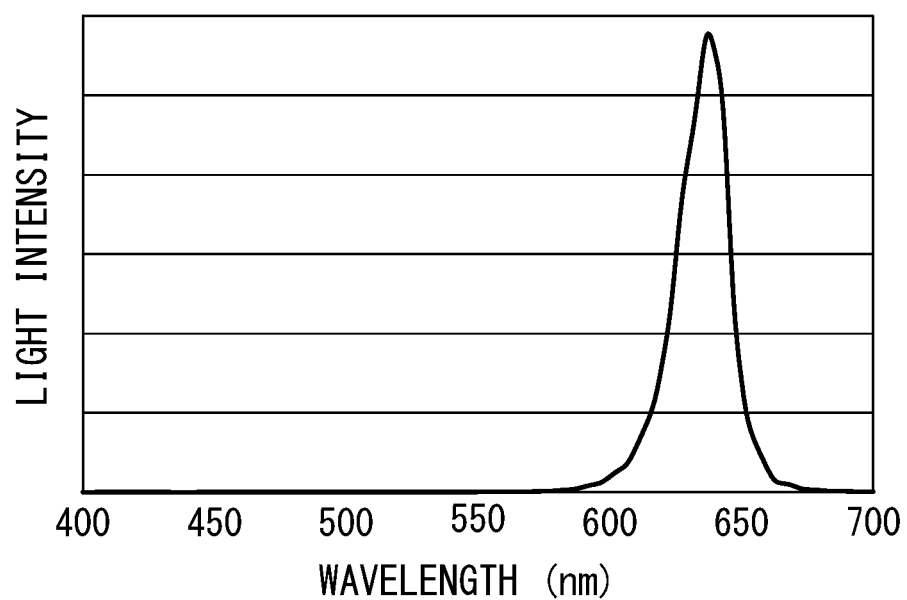
FIG. 15C is a graph illustrating the spectral characteristic of an LED on the shortest optical path in the endoscope light source device illustrated in FIG. 14.
Figure 17A:
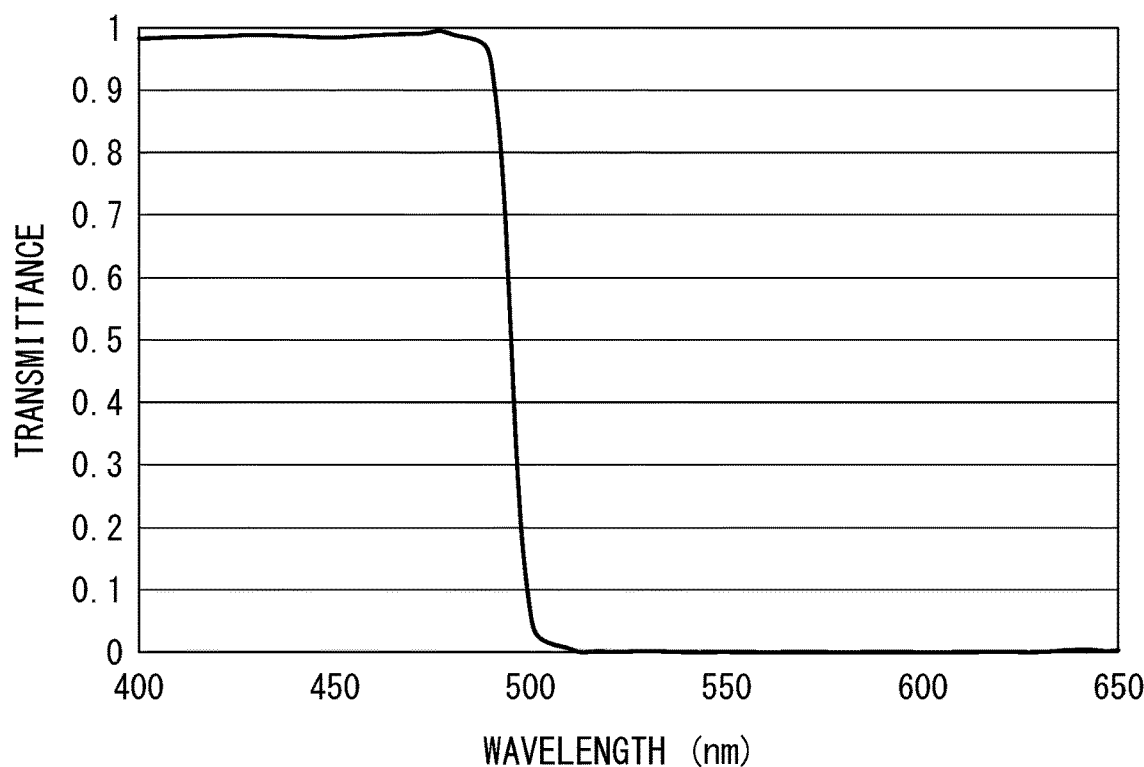
FIG. 17A is a graph illustrating a transmittance characteristic of a dichroic mirror on the second-longest optical path in the endoscope light source device illustrated in FIG. 14.
Figure 17B:
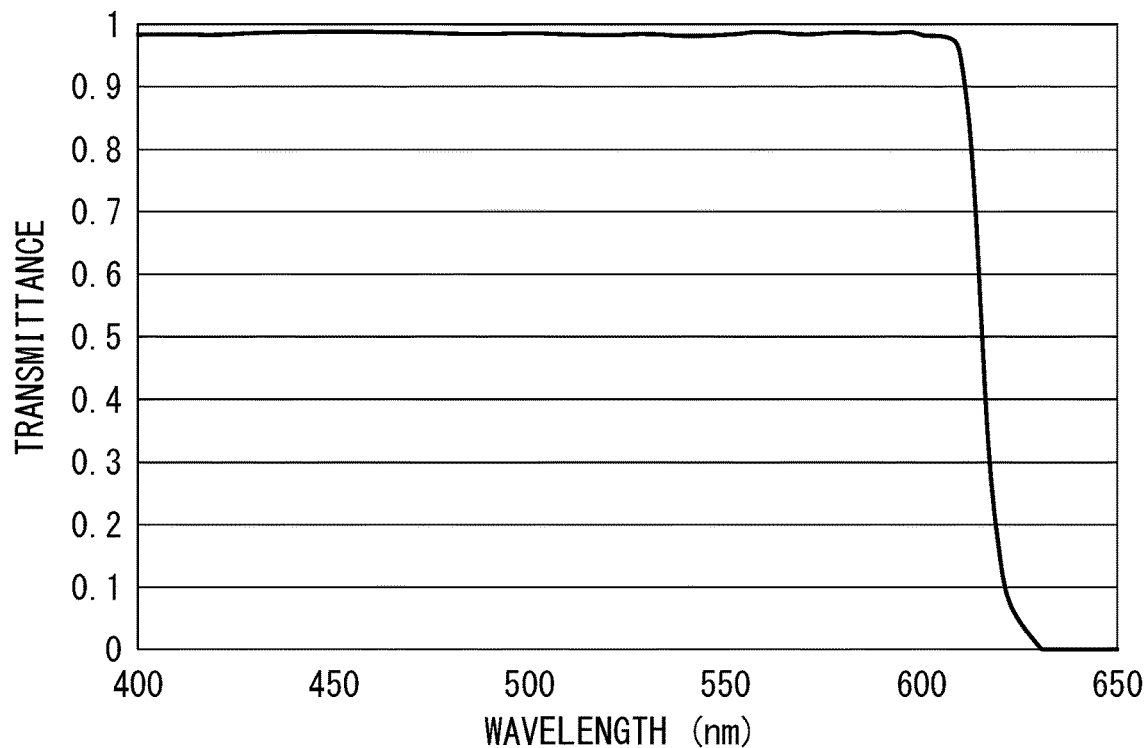
FIG. 17B is a graph illustrating a transmittance characteristic of a dichroic mirror on the shortest optical path in the endoscope light source device illustrated in FIG. 14.
Figure 18:
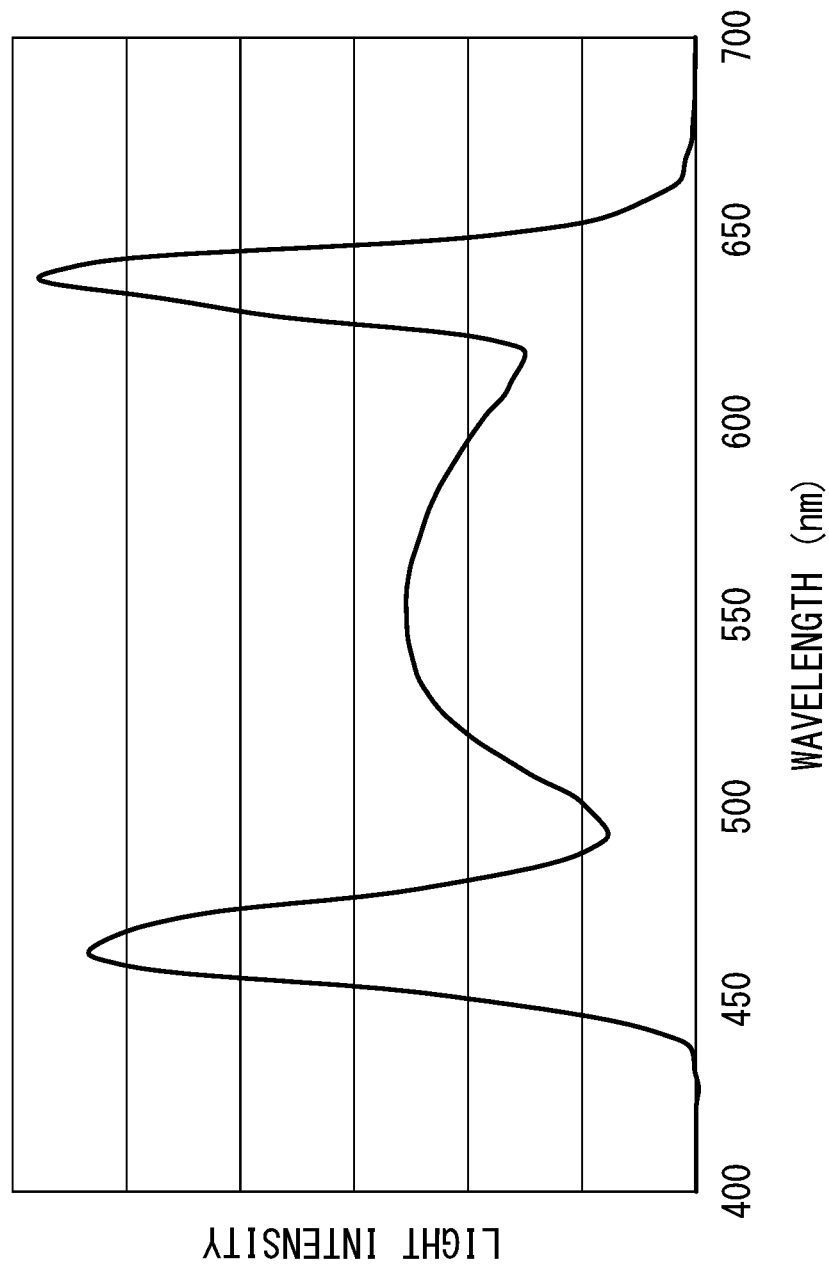
FIG. 18 is a graph illustrating a spectral characteristic of a light source emitted light of the endoscope light source device illustrated in FIG. 14.

The LEDs having spectral characteristics shown in FIGS. 15A to 15C are respectively used as the LEDs 1, 2, and 3, a mirror having a reflectance characteristic shown in FIG. 16 is used as the mirror 6, dichroic mirrors having the transmittance characteristics shown in FIGS. 17A and 17B are respectively used as the dichroic mirrors 4, and the light source emitted light has the spectral characteristic shown in FIG. 18.

The aperture size φ of the diaphragm 5 placed on the longest optical path is 34 mm, the distance L is 12.55 mm, the paraxial magnification absolute value β is 0.91, and the numerical aperture NA of the light guide fiber of the endoscope is 0.5. In this manner, $\phi/L=2.71$ and $1.5\text{NA}\beta/\sqrt{(1-(\text{NA}\beta)^2)}=0.98$. Thus, conditional formula (6) is satisfied.

The aperture size $\phi$ of the diaphragm 5 placed on the second-longest optical path is 29 mm, the distance L is 12.55 mm, the paraxial magnification absolute value $\beta$ is 0.94, and the numerical aperture NA of the light guide fiber of the endoscope is 0.5. In this manner, $\phi/L=2.31$ and $1.5\text{NA}\beta/\sqrt{(1-(\text{NA}\beta)^2)}=1.02$. Thus, conditional formula (6) is satisfied.

The aperture size $\phi$ of the diaphragm 5 placed on the shortest optical path is 21 mm, the distance L is 12.55 mm, the paraxial magnification absolute value $\beta$ is 0.94, and the numerical aperture NA of the light guide fiber of the endoscope is 0.5. In this manner, $\phi/L=1.67$, and $1.5\text{NA}\beta/\sqrt{(1-(\text{NA}\beta)^2)}=1.10$. Thus, conditional formula (6) is satisfied.

Third Embodiment

A third embodiment of the endoscope light source device 10 according to the present embodiment will now be described.

In this embodiment, as illustrated in FIG. 8, three LEDs 1, 2, and 3 are provided, and a diaphragm 5 is disposed between each of the LEDs 1, 2, and 3 and the corresponding collimating lens 11.

The spectral characteristics of the LEDs 1, 2, and 3, the reflectance characteristic of the mirror 6, the transmittance characteristics of the dichroic mirrors 4, and the spectral characteristic of the light source emitted light are the same as those in the second embodiment.

The aperture size $\phi$ of the diaphragm 5 placed on the longest optical path is 21 mm, the distance L is 7.75 mm, the paraxial magnification absolute value $\beta$ is 0.91, and the numerical aperture NA of the light guide fiber of the endoscope is 0.5. In this manner, $\phi/L=2.71$ and $1.5\text{NA}\beta/\sqrt{(1-(\text{NA}\beta)^2)}=0.98$. Thus, conditional formula (6) is satisfied.

The aperture size $\phi$ of the diaphragm 5 placed on the second-longest optical path is 21 mm, the distance L is 9.09 mm, the paraxial magnification absolute value $\beta$ is 0.94, and the numerical aperture NA of the light guide fiber of the endoscope is 0.5. In this manner, $\phi/L=2.31$ and $1.5\text{NA}\beta/\sqrt{(1-(\text{NA}\beta)^2)}=1.02$. Thus, conditional formula (6) is satisfied.

The aperture size $\phi$ of the diaphragm 5 placed on the shortest optical path is 21 mm, the distance L is 12.55 mm, the paraxial magnification absolute value $\beta$ is 0.94, and the numerical aperture NA of the light guide fiber of the endoscope is 0.5. In this manner, $\phi/L=1.67$, and $1.5\text{NA}\beta/\sqrt{(1-(\text{NA}\beta)^2)}=1.10$. Thus, conditional formula (6) is satisfied.

As a result, the above-described embodiments also lead to the following aspects.

An aspect of the present invention is directed to an endoscope light source device that includes a plurality of solid-state light sources; a plurality of collimating lenses that respectively collimate light beams emitted from the solid-state light sources into substantially parallel light beams; a multiplexing optical member that multiplexes the light beams that have been collimated into substantially parallel light beams by the collimating lenses; a light level-adjusting mechanism that is disposed between at least one of the solid-state light sources and at least one of the collimating lens and that can adjust the quantity of peripheral light from the solid-state light source; and a focusing lens that focuses light beams from the solid-state light sources multiplexed by the multiplexing optical member and causes the light beams to enter an end surface of a light guide of an endoscope.

According to this aspect, after light beams respectively emitted from the solid-state light sources are converted into substantially parallel light beams by the collimating lenses, the substantially parallel light beams are multiplexed by the multiplexing optical member, are focused through the focusing lens, and enter another surface of a light guide of the endoscope. The light level-adjusting mechanism disposed between the at least one solid-state light source and the at least one collimating lens adjusts the quantity of the peripheral light from the solid-state light source, and the resulting light beam enters the collimating lens. As a result, the quantity of peripheral light can be adjusted for each of the solid-state light source.

In other words, even when the thickness of the light guide is changed by replacing the scope of the endoscope, the light-level balance of the light beams from the solid-state light sources can remain unchanged. In particular, when light sources that emit light beams having different wavelengths are employed as the solid-state light sources, it becomes possible to prevent emission of light beams having different color balance depending on the thickness of the light guide and to improve the color reproducibility.

In the aspect described above, the light level-adjusting mechanism may block more peripheral light when an optical path length from each of the solid-state light source to the focusing lens is shorter.

In this manner, since the focusing lens causes clipping of more peripheral light as the optical path length increases, the quantity of the light from the solid-state light source having a large optical path length decreases and the light-level balance is degraded as the light guide of the installed scope becomes thicker unless the light level-adjusting mechanism is installed. By placing the light level-adjusting mechanism to block more peripheral light as the optical path length decreases, degradation of the light-level balance of the light beam from the solid-state light source having a large optical path length is prevented and the light-level balance can remain constant even when the light guide of the installed scope is thick.

In the aspect described above, the light level-adjusting mechanism may be a diaphragm that has a different aperture size for each combination of the solid-state light source and the collimating lens.

In this manner, by decreasing the aperture size of the installed diaphragm such that more peripheral light from the solid-state light source is blocked as the optical path length decreases, degradation of the light-level balance of the light beam from the solid-state light source having a large optical path length is prevented and the light-level balance can remain constant when the light guide of the installed scope is thick.

In the aspect described above, the light level-adjusting mechanism may be a diaphragm with which a distance between the diaphragm and the solid-state light source is different for each combination of the solid-state light source and the collimating lens.

In this manner, by placing the diaphragm, which is installed to block more peripheral light from the solid-state light source as the optical path length decreases, far from the solid-state light source, degradation of the light-level balance of the light beam from the solid-state light source having a large optical path length is prevented and the light-level balance can remain constant even when the light guide of the installed scope is thick.

In the aspect described above, the diaphragm may satisfy the following conditional formula:

$$\phi/L \geq 1.5\text{NA}\beta/\sqrt{(1-\text{NA}\beta)^2)}$$

where $\phi$ represents an aperture size of the diaphragm, NA represents a numerical aperture of the light guide, $\beta$ represents an absolute value of a paraxial magnification when the solid-state light source forms an image in the light guide, and L represents an optical path length between the solid-state light source and the diaphragm.

In this manner, light distribution with little color nonuniformity that does not obstruct observation can be obtained.

The present invention has an advantageous effect in that variation of the color balance of light beams emitted from tips of scopes can be suppressed even when scopes having different light guide diameters are used in combination.

REFERENCE SIGNS LIST 1, 2, 3 LED (solid-state light source)
4 dichroic mirror (multiplexing optical member)
5 diaphragm (light level-adjusting mechanism)
7 focusing lens
8 light guide
10 endoscope light source device
11 collimating lens
L distance

The invention claimed is:

1. An endoscope light source device comprising:
a plurality of solid-state light sources;
a plurality of collimating lenses that respectively collimate light beams emitted from the plurality of solid-state light sources into substantially parallel light beams;
a multiplexing optical member that multiplexes the light beams that have been collimated into substantially parallel light beams by the plurality of collimating lenses;
at least one diaphragm disposed between at least one of the plurality of solid-state light sources and a corresponding at least one of the plurality of collimating lenses; and
a focusing lens that focuses light beams from the plurality of solid-state light sources multiplexed by the multiplexing optical member and causes the light beams to enter an end surface of a light guide of an endoscope,
wherein the at least one diaphragm blocks more peripheral light as an optical path length from each of the plurality of solid-state light sources to the focusing lens becomes smaller.

2. The endoscope light source device according to claim 1, wherein the at least one diaphragm has a different aperture size for each combination of one of the plurality of solid-state light sources and a corresponding one of the plurality of collimating lenses.

3. The endoscope light source device according to claim 2, wherein the at least one diaphragm satisfies a conditional formula below:

$\phi/L \geq 1.5 NA\beta/\sqrt{(1-(NA\beta)^2)}$ where
$\phi$ represents an aperture size of the at least one diaphragm,
NA represents a numerical aperture of the light guide,
$\beta$ represents an absolute value of a paraxial magnification when a corresponding at least one of the plurality of solid-state light sources forms an image in the light guide, and
L represents an optical path length between the at least one diaphragm and the corresponding at least one of the plurality of solid-state light sources.

4. The endoscope light source device according to claim 1, wherein a distance between the at least one diaphragm and a corresponding at least one of the plurality of solid-state light sources is different for each combination of one of the plurality of solid-state light sources and a corresponding one of the collimating lenses.

5. An endoscope light source device comprising:
a plurality of solid-state light sources;
a plurality of collimating lenses that respectively collimate light beams emitted from the plurality of solid-state light sources into substantially parallel light beams;
a multiplexing optical member that multiplexes the light beams that have been collimated into substantially parallel light beams by the plurality of collimating lenses;
at least one diaphragm disposed between at least one of the plurality of solid-state light sources and a corresponding at least one of the collimating lenses; and
a focusing lens that focuses light beams from the plurality of solid-state light sources multiplexed by the multiplexing optical member and causes the light beams to enter an end surface of a light guide of an endoscope,
wherein the at least one diaphragm has a different aperture size for each combination of one of the plurality of solid-state light sources and a corresponding one of the plurality of collimating lenses, and, as an optical path length from each of the plurality of solid-state light sources to the focusing lens becomes smaller, the aperture size of the at least one diaphragm becomes smaller.

6. The endoscope light source device according to claim 5, wherein the at least one diaphragm comprises a plurality of diaphragms,
the plurality of diaphragms are respectively disposed between the plurality of solid-state light sources and the plurality of collimating lenses, and
distances between the plurality of solid-state light sources and the respective plurality of diaphragms are the same.

7. The endoscope light source device according to claim 5, wherein the at least one diaphragm satisfies a conditional formula below:

$\phi/L \geq 1.5 NA\beta/\sqrt{(1-(NA\beta)^2)}$ where
$\phi$ represents an aperture size of the at least one diaphragm,
NA represents a numerical aperture of the light guide,
$\beta$ represents an absolute value of a paraxial magnification when a corresponding at least one of the plurality of solid-state light sources forms an image in the light guide, and
L represents an optical path length between the at least one diaphragm and the corresponding at least one of the plurality of solid-state light sources.

8. An endoscope light source device comprising:
a plurality of solid-state light sources;
a plurality of collimating lenses that respectively collimate light beams emitted from the plurality of solid-state light sources into substantially parallel light beams;
a multiplexing optical member that multiplexes the light beams that have been collimated into substantially parallel light beams by the plurality of collimating lenses;
at least one diaphragm disposed between at least one of the plurality of solid-state light sources and a corresponding at least one of the plurality of collimating lenses; and
a focusing lens that focuses light beams from the plurality of solid-state light sources multiplexed by the multiplexing optical member and causes the light beams to enter an end surface of a light guide of an endoscope, wherein a distance between the at least one diaphragm and a corresponding at least one of the plurality of solid-state light sources is different for each combination of one of the plurality of solid-state light sources and a corresponding one of the collimating lenses, and as an optical path length from each of the solid-state light source to the focusing lens becomes smaller, the distance from the at least one diaphragm to a corresponding at least one of the plurality of solid-state light source becomes larger.

9. The endoscope light source device according to claim 8, wherein the at least one diaphragm comprises a plurality of diaphragms,
the plurality of diaphragms are respectively disposed between the plurality of solid-state light sources and the plurality of collimating lenses, and
aperture sizes of the plurality of diaphragms are the same.

10. The endoscope light source device according to claim 8, wherein the at least one diaphragm satisfies a conditional formula below:

$$\phi/L \geq 1.5 NA\beta/\sqrt{(1-(NA\beta)^2)}$$

where
$\phi$ represents an aperture size of the at least one diaphragm,
NA represents a numerical aperture of a light guide,
$\beta$ represents an absolute value of a paraxial magnification when a corresponding at least one of the plurality of solid-state light sources forms an image in the light guide, and
L represents an optical path length between the at least one diaphragm and the corresponding at least one of the plurality of solid-state light sources.

* * * * *